US 6,533,817 B1

(12) United States Patent  
Norton et al.

(10) Patent No.: US 6,533,817 B1
(45) Date of Patent: Mar. 18, 2003

(54) PACKAGED, PARTIALLY HYDRATED PROSTHETIC DISC NUCLEUS

(75) Inventors: Britt K. Norton, Eden Prairie, MN (US); Tara N. Sherman, Cottage Grove, MN (US); Laura J. Bauer, Edina, MN (US)

(73) Assignee: Raymedica, Inc., Bloomington, MN (US)

( * ) Notice: Subject to any disclaimer, the term of this patent is extended or adjusted under 35 U.S.C. 154(b) by 0 days.

(21) Appl. No.: 09/587,159

(22) Filed: Jun. 5, 2000

(51) Int. Cl.[7] ................................................ A61F 2/44
(52) U.S. Cl. ............................ 623/17.16; 623/17.12; 623/17.11
(58) Field of Search ................... 206/438; D9/314, D9/424, 499; 28/289, 299; 623/16.11, 11.11, 17.11, 17.16, 17.12; 606/61

(56) References Cited

U.S. PATENT DOCUMENTS

| | | |
|---|---|---|
| 3,867,728 A | 2/1975 | Stubstad et al. |
| 3,875,595 A | 4/1975 | Froning |
| 3,883,902 A | 5/1975 | Lynch |
| 4,772,287 A | 9/1988 | Ray et al. |
| 4,863,477 A | 9/1989 | Monson |
| 4,904,260 A | 2/1990 | Ray et al. |
| 4,932,969 A | 6/1990 | Frey et al. |
| 5,047,055 A | 9/1991 | Bao et al. |
| 5,171,280 A | 12/1992 | Baumgartner |
| 5,192,326 A | 3/1993 | Bao et al. |
| 5,458,643 A | 10/1995 | Oka et al. |

(List continued on next page.)

FOREIGN PATENT DOCUMENTS

| | | |
|---|---|---|
| DE | 39 22 203 | 10/1990 |
| EP | 0 700 671 A1 | 3/1996 |
| FR | 2 639 823 | 6/1990 |
| WO | WO 96/11642 | 4/1996 |
| WO | WO 99/62439 | 12/1999 |
| WO | WO 00/64385 | 11/2000 |

OTHER PUBLICATIONS

D. Charles D. Ray; "The Artificial Disc—Introduction, History, and Socioeconomics"; ©1992, pp. 205–225.
A copy of PCT International Search Report for International Application No. PCT/US01/17468, mailed on Jan. 3, 2002 (8 pages).

Primary Examiner—Corrine McDermott
Assistant Examiner—Umi Chattopadhyay
(74) Attorney, Agent, or Firm—Dicke, Billig & Czaja, P.A.

(57) ABSTRACT

A packaged prosthetic disc nucleus including a prosthetic disc nucleus and a retainer. The prosthetic disc nucleus includes a hydrogel core formed to hydrate from a dehydrated state. Further, the prosthetic disc nucleus is configured to such that following implantation into a nucleus cavity, the hydrogel core hydrates to a final hydrated state. The retainer selectively contains the prosthetic disc nucleus. Further, upon contact with a hydration liquid, the retainer is configured to allow the hydrogel core to hydrate from the dehydrated state while preventing the hydrogel core from hydrating to the final hydrated state. Thus, the prosthetic disc nucleus is constrained by the retainer in a partially hydrated state. In one preferred embodiment, the combination prosthetic disc nucleus/retainer is sealed within an outer enclosure, such as a pouch, that also contains a hydration liquid for hydrating the hydrogel core. During use, the prosthetic disc nucleus is removed from the retainer and implanted in the partially hydrated state.

29 Claims, 7 Drawing Sheets

U.S. PATENT DOCUMENTS

| | | |
|---|---|---|
| 5,534,028 A | 7/1996 | Bao et al. |
| 5,562,736 A | 10/1996 | Ray et al. |
| 5,645,597 A | 7/1997 | Krapiva |
| 5,649,945 A | 7/1997 | Ray et al. |
| 5,665,111 A | 9/1997 | Ray et al. |
| 5,674,295 A | 10/1997 | Ray et al. |
| 5,705,780 A | 1/1998 | Bao |
| 5,800,549 A | 9/1998 | Bao et al. |
| 5,824,093 A | 10/1998 | Ray et al. |
| 5,865,845 A | 2/1999 | Thalgott |
| 5,888,220 A | 3/1999 | Felt et al. |
| 5,919,235 A | 7/1999 | Husson et al. |
| 5,961,554 A | 10/1999 | Janson et al. |
| 5,976,186 A | 11/1999 | Bao et al. |
| 6,022,376 A | 2/2000 | Assell et al. |
| 6,066,325 A | 5/2000 | Wallace et al. |
| 6,113,639 A * | 9/2000 | Ray et al. ............... 623/17.16 |
| 6,132,465 A | 10/2000 | Ray et al. |

\* cited by examiner

PACKAGED, PARTIALLY HYDRATED PROSTHETIC DISC NUCLEUS

BACKGROUND OF THE INVENTION

The present invention relates to a prosthetic disc nucleus. More particularly, it relates to a hydrophilic prosthetic spinal disc nucleus packaged and provided to surgeons in a partially hydrated state.

The vertebral spine is the axis of the skeleton upon which all of the body parts "hang". In humans, the normal spine has seven cervical, twelve thoracic and five lumbar segments. The lumbar segments sit upon a sacrum, which then attaches to a pelvis, in turn supported by hip and leg bones. The bony vertebral bodies of the spine are separated by intervertebral discs, which act as joints, but allow known degrees of flexion, extension, lateral bending and axial rotation.

The typical vertebra has a thick interior bone mass called the vertebral body, and a neural (vertebral) arch that arises from a posterior surface of the vertebral body. Each narrow arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch that extends posteriorly and acts to protect a posterior side of the spinal cord is known as the lamina. Projecting from the posterior region of the neural arch is a spinous process. The central portions of adjacent vertebrae are each supported by an intervertebral disc.

The intervertebral disc primarily serves as a mechanical cushion between the vertebral bones, permitting controlled motions within vertebral segments of the axial skeleton. The normal disc is a unique, mixed structure, comprised of three component tissues: the nucleus pulposus ("nucleus"), the anulus fibrosus ("anulus"), and two opposing vertebral end plates. The two vertebral end plates are each composed of thin cartilage overlying a thin layer of hard, cortical bone which attaches to the spongy, richly vascular, cancellous bone of the vertebral body. The end plates thus serve to attach adjacent vertebrae to the disc. In other words, a transitional zone is created by the end plates between the malleable disc and the bony vertebrae.

The anulus of the disc is a tough, outer fibrous ring that binds together adjacent vertebrae. This fibrous portion, which is much like a laminated automobile tire, is generally about 10 to 15 millimeters in height and about 15 to 20 millimeters in thickness. The fibers of the anulus consist of 15 to 20 overlapping multiple plies, and are inserted into the superior and inferior vertebral bodies at roughly a 30-degree angle in both directions. This configuration particularly resists torsion, as about half of the angulated fibers will tighten when the vertebrae rotate in either direction, relative to each other. The laminated plies are less firmly attached to each other.

Immersed within the anulus, positioned much like the liquid core of a golf ball, is the nucleus. The anulus and opposing end plates maintain a relative position of the nucleus in what can be defined as a nucleus cavity. The healthy nucleus is largely a gel-like substance having a high water content, and similar to air in a tire, serves to keep the anulus tight yet flexible. The nucleus-gel moves slightly within the anulus when force is exerted on the adjacent vertebrae with bending, lifting, etc.

The nucleus and the inner portion of the anulus have no direct blood supply. In fact, the principal nutritional source for the central disc arises from circulation within the opposing vertebral bodies. Microscopic, villous-like fingerlings of the nuclear and anular tissue penetrate the vertebral end plates and allow fluids to pass from the blood across the cell membrane of the fingerlings and then inward to the nuclear tissue. These fluids are primarily body water and the smallest molecular weight nutrients and electrolytes.

The natural physiology of the nucleus promotes these fluids being brought into, and released from, the nucleus by cyclic loading. When fluid is forced out of the nucleus, it passes again through the end plates and then back into the richly vascular vertebral bodies. The cyclic loading amounts to daily variations in applied pressure on the vertebral column (e.g., body weight and muscle pull) causing the nucleus to expel fluids, followed by periods of relaxation and rest, resulting in fluid absorption or swelling by the nucleus. Thus, the nucleus changes volume under loaded and non-loaded conditions. Further, the resulting tightening and loosening effect on the anulus stimulates the normal anulus collagen fibers to remain healthy or to regenerate when torn, a process found in all normal ligaments related to body joints. Notably, the ability of the nucleus to release and imbibe fluids allows the spine to alter its height and flexibility through periods of loading or relaxation. Normal loading cycling is thus an effective nucleus and inner anulus tissue fluid pump, not only bringing in fresh nutrients, but perhaps more importantly, removing the accumulated, potentially autotoxic by-products of metabolism.

The spinal disc may be displaced or damaged due to trauma or a disease process. A disc herniation occurs when the anulus fibers are weakened or torn and the inner tissue of the nucleus becomes permanently bulged, distended, or extruded out of its normal, internal anular confines. The mass of a herniated or "slipped" nucleus can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases, causing the anulus to buckle in areas where the laminated plies are loosely bonded. As these overlapping laminated plies of the anulus begin to buckle and separate, either circumferential or radial anular tears may occur, which may contribute to persistent and disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate pain from degenerated or herniated discs, the nucleus is removed and the two adjacent vertebrae are surgically fused together. While this treatment alleviates the pain, all discal motion is lost in the fused segment. Ultimately, this procedure places greater stress on the discs adjacent the fused segment as they compensate for the lack of motion, perhaps leading to premature degeneration of those adjacent discs. A more desirable solution entails replacing in part or as a whole the damaged nucleus with a suitable prosthesis having the ability to complement the normal height and motion of the disc while stimulating the natural disc physiology.

The first prostheses embodied a wide variety of ideas, such as ball bearings, springs, metal spikes and other perceived aids. These prosthetic discs were designed to replace the entire intervertebral disc space, and were large and rigid. Beyond the questionable efficacy of those devices were the inherent difficulties encountered during implantation. Due to their size and inflexibility, these first generation devices required an anterior implantation approach as the barriers presented by the lamina and, more importantly, the spinal cord and nerve rootlets during posterior implantation, could not be avoided. Recently, smaller and more flexible prosthetic nucleus devices have been developed. With the reduction in prosthesis size, the ability to work around the spinal cord and nerve rootlets during posterior implantation has become possible.

Generally speaking, these reduced sized prostheses are intended to serve as a replacement for the natural nucleus. In other words, the anulus and end plates remain intact, and the prosthesis is implanted into the nucleus cavity through an opening formed in the anulus. To minimize damage or stress on the anulus during implantation, the prosthetic nucleus will preferably expand from a relatively small pre-implant size to a relatively larger post-implant size. In this regard, hydrogel materials have been identified as being highly applicable. Generally speaking, hydrogel materials have a strong affinity for water, and expand upon hydration. With this in mind, a hydrogel-based prosthetic nucleus can be implanted in a relatively small, dehydrated state. Once in contact with the fluids found in the intervertebral disc space the hydrogel will hydrate. With hydration, the hydrogel-based prosthetic nucleus will grow or expand, forcing apart the adjacent vertebrae. When fully hydrated, then, the hydrogel-based prosthetic nucleus has properties highly similar to a natural nucleus, restoring and maintaining the height of a damaged disc space, and tightening the anulus.

Several different potential hydrogel-based prosthetic nucleus devices are described, for example, in Ray et al., U.S. Pat. No. 5,647,295 and Bao et al., U.S. Pat. No. 5,047,055, the teachings of which are incorporated herein by reference. Regardless of exact design, the hydrogel-based prosthesis is dehydrated prior to implant, rendering the device as small as possible. Following implant, the hydrogel material will slowly hydrate to a final hydration level, normally over the course of two or three days. Because the time for hydration is relatively lengthy, the possibility of prosthesis migration or explant back through the anulus opening may arise. In other words, in the dehydrated state, the hydrogel-based prosthetic nucleus has, in theory, a height and width slightly smaller than a height and width of the anulus opening. Because the hydrogel material does not immediately hydrate, and therefore expand, the outer dimensions of the prosthesis continue to correspond with the dimensions of the anulus opening. Therefore, the anulus cannot readily prevent the hydrogel-based prosthetic nucleus from migrating back through the anulus opening. Even if this opening is closed via sutures following implant, various forces acting upon the spine have the potential to "push" the prosthesis back through the anulus opening. In this regard, the hydrogel material is extremely hard in the dehydrated state, thereby increasing the likelihood of spontaneous explant. That is to say, the absence of device conformability promotes sliding of the prosthesis within the nucleus cavity with the placement of a load and/or opposing movement of the end plates.

Additionally, it is often times difficult to implant a properly sized hydrogel-based prosthesis. In theory, a surgeon will evaluate the disc space and select a correspondingly sized prosthetic device. Several factors may impede the surgeon's ability to implant the so-selected device. First, the implant environment is highly confined, making access to, and maneuvering within, the disc space exceedingly difficult. Also, while the hydrogel-based prosthesis is dehydrated prior to implant, an absolute limit or minimum dehydration size/volume exists. Thus, for example, the Bao device is shown as being extremely small in the dehydrated state, expanding to fill the entire nucleus cavity with hydration. In practice, current hydrogel technology does not allow for such a drastic change (e.g., on the order of 10×) in volume. Instead, a hydrogel-based prosthesis can only experience a maximum increase in volume (from the dehydrated state to a fully hydrated state) on the order of 2×. As a result, although the disc space size may be approximated accurately, the corresponding prosthesis device may be too large (in a dehydrated state) to be implanted. Additionally, while the natural nucleus material is desirably completely removed, this is nearly impossible to accomplish, thereby decreasing the implant space. Taken in combination, the above-factors may force the surgeon to instead implant a prosthetic device that is less than optimally sized. Unfortunately, the reduced-sized prosthesis is likely more susceptible to unwanted migration, and may not provide proper discal support.

Degenerated, painfully disabling intra-spinal discs are a major economic and social problem for patients, their families, employers and the public at large. Any significant means to correct these conditions without further destruction or fusion of the disc may therefore serve an important role. Other means to replace the function of a degenerated disc have major problems such as complex surgical procedures, unproven efficacy, placing unnecessary and possibly destructive forces on an already damaged anulus, etc. Further, unexpected migration and explant of the prosthesis, especially a hydrogel-based prosthetic nucleus, from the disc space following implant, while uncommon, may be a potential concern. Therefore, a need exists for a prosthetic spinal disc nucleus implantable in a form having improved conformability and a reduced potential for explant.

SUMMARY OF THE INVENTION

One aspect of the present invention relates to a packaged prosthetic disc nucleus. The packaged prosthetic disc nucleus includes a prosthetic disc nucleus and a retainer. The prosthetic disc nucleus is sized for implantation within a nucleus cavity and includes a hydrogel core configured to hydrate from a dehydrated state to a final hydrated state, such as following implant. The retainer selectively contains the prosthetic disc nucleus. Further, upon contact with a hydration liquid, the retainer is configured to allow the hydrogel core to hydrate from the dehydrated state, but prevents the hydrogel core from hydrating to the final hydrated state. For example, in one preferred embodiment, the packaged prosthetic disc nucleus further includes an outer enclosure, such as a pouch, surrounding the retainer and a hydration liquid contained within the enclosure for hydrating the hydrogel core. Regardless of the hydration liquid source, the prosthetic disc nucleus is constrained by the retainer to a partially hydrated state. More particularly, the retainer limits volumetric expansion of the hydrogel core, thereby constraining hydration to the partially hydrated state. During use, the prosthetic disc nucleus is removed from the retainer and preferably implanted within a nucleus cavity in the partially hydrated state. The hydrogel core then hydrates to the final hydrated state by imbibing fluids from within the nucleus cavity. Because the hydrogel core is partially hydrated, the prosthetic disc nucleus has improved cnoformability and will reach the final hydrated state more quickly than a similar prosthetic disc nucleus implanted in a dehydrated state.

Another aspect of the present invention relates to a packaged prosthetic disc nucleus. The packaged prosthetic disc nucleus is sized for implantation within a nucleus cavity and includes a prosthetic disc nucleus and a retainer. The prosthetic disc nucleus includes a hydrogel core configured to hydrate and expand from a dehydrated height to a final hydration height. The retainer selectively contains the prosthetic disc nucleus. When placed in contact with a hydration liquid, the retainer allows the hydrogel core to hydrate and expand from the dehydrated height, but prevents the hydrogel core from attaining the final hydration height. In one preferred embodiment, for example, the packaged device farther includes an outer pouch containing the retainer and a supply of hydration liquid in contact with the prosthetic nucleus. Regardless, with hydration liquid interaction, the retainer is configured to constrain the hydrogel core to a partial hydration height that is less than the final hydration height. During use, the prosthetic disc nucleus, at the partial hydration height, is removed from the retainer and implanted into the nucleus cavity. Because the partial hydration height is less than the final hydration height, a size of a requisite opening in the anulus can be reduced. Further, in accordance with one preferred embodiment, the retainer dictates that the partial hydration height is less than a natural or unloaded dehydrated height, thereby promoting selection and implantation of a properly sized prosthesis.

Yet another aspect of the present invention provides a method of packaging a prosthetic disc nucleus including a hydrogel core. The hydrogel core is configured to hydrate from a dehydrated level for subsequent implantation within the nucleus cavity where the hydrogel hydrates to a final hydration level. The method includes dehydrating the hydrogel core. A retainer is provided forming a cavity sized to selectively contain the prosthetic disc nucleus. The prosthetic disc nucleus is placed within the cavity. The combination prosthetic disc nucleus/retainer is then allowed unimpeded contact with a hydration liquid such that the hydrogel core hydrates. In one preferred embodiment, the combination retainer/prosthetic disc nucleus is placed within an outer enclosure. The outer enclosure is then at least partially filled with the liquid for hydrating the hydrogel core. Finally, the outer enclosure is sealed for subsequent delivery to a surgeon. Regardless of the source, the retainer constrains expansion and therefore hydration of the hydrogel core to a partial hydration level that is less than the final hydration level.

DESCRIPTION OF THE PREFERRED EMBODIMENTS

Figure 1:
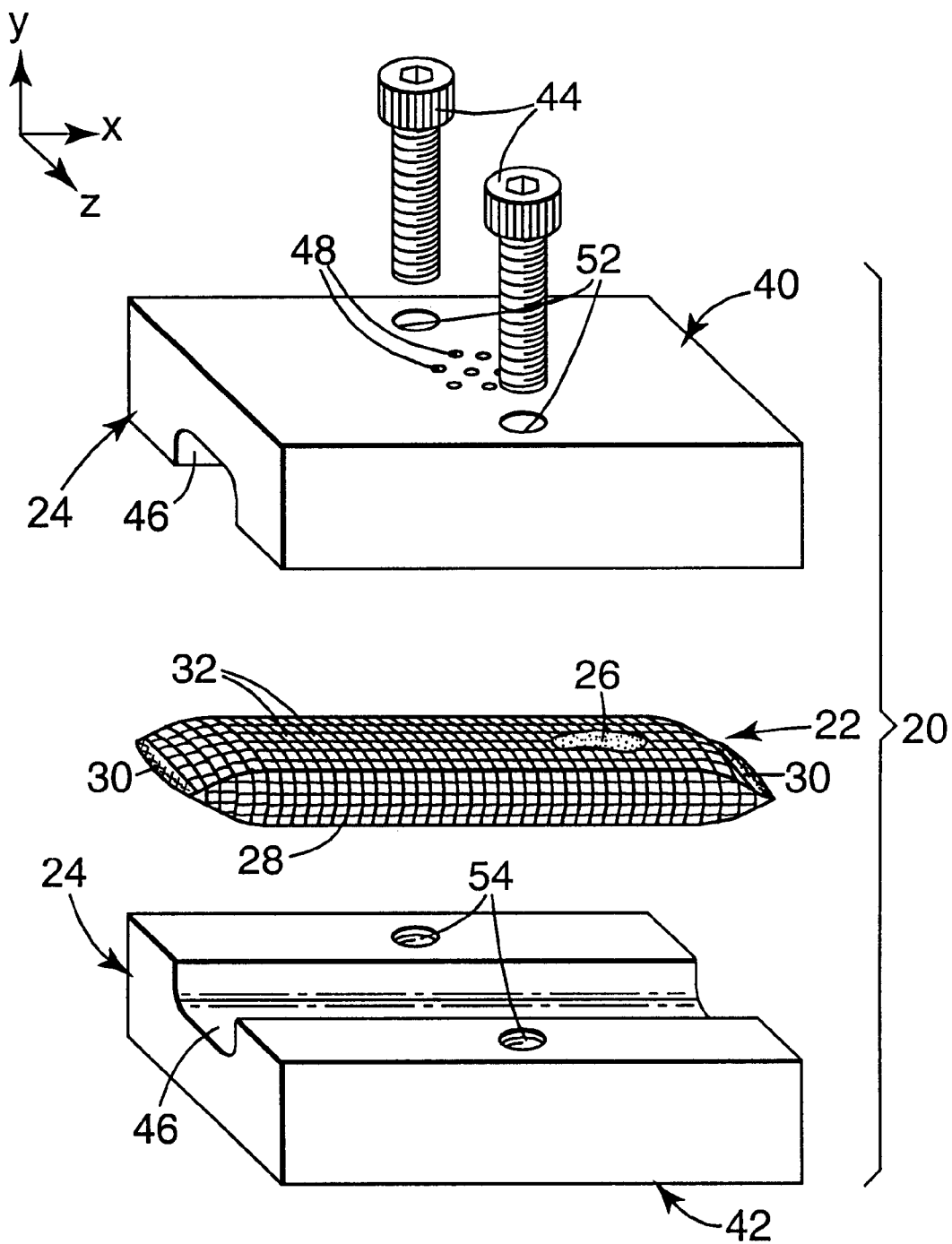
FIG. 1 is an exploded, perspective view of a packaged prosthetic disc nucleus in accordance with the present invention.

One preferred embodiment of a packaged prosthetic disc nucleus 20 is shown in FIG. 1. The packaged prosthetic disc nucleus 20 includes a prosthetic disc nucleus 22 and a retainer 24. As described in greater detail below, the retainer 24 selectively maintains the prosthetic nucleus 22 in a partially hydrated state.

The prosthetic disc nucleus 22 can assume a wide variety of forms, but includes a hydrogel core 26. Generally speaking, the hydrogel material is able to hydrate (imbibe water), and to dehydrate (release water), expanding and contracting in size, respectively. As used throughout this specification, then, the hydrogel core 26 is described with reference to three different hydration states or levels; including a dehydrated state or level, a partially hydrated state or level and a final hydrated state or level. The "dehydrated state" is in reference to the hydrogel core 26 retaining only a negligible amount of water. For example, if left exposed to air and/or placed in an oven, water will evaporate or be released from the hydrogel core 26 until an equilibrium "dehydration state" water content of less than approximately 10% by weight is realized. Conversely, the "final hydrated state" is in reference to the hydrogel core 26 imbibing and retaining as much water as possible for the particular hydrogel material formulation. Notably, the "final hydrated state" water content may or may not be equivalent to a water content of a theoretical full or complete hydration of the hydrogel core 26, depending upon an overall construction of the prosthetic disc nucleus 22. For example, with reference to the one preferred embodiment of FIG. 1 and as described below, a constraining jacket 28 constrains and prevents the hydrogel core 26 from achieving full or complete hydration. In other words, following implantation, the hydrogel core 26 will hydrate and expand to the limits of the constraining jacket 28. At this point, the constraining jacket 28 prevents further expansion, such that the hydrogel core 26 cannot imbibe additional water and is thus in a "final hydrated state". Alternatively, where the constraining jacket 28 is of a size and/or construction different from that shown in FIG. 1 (e.g., enlarged volume and/or elastic material), or where the constraining jacket 28 is eliminated entirely, the hydrogel core 26 is unconstrained and the final hydrated state of the hydrogel core 26 can be equal to full or complete hydration. As a point of reference, the hydrogel core 26 can be formulated to have a water content of 90% of its dehydrated or dry weight in a theoretical, unconstrained, fully hydrated state. However, the constraining jacket 28 may limit the final hydrated state of hydrogel core 26 to a water content of 80% of its dehydrated weight. Regardless, "final hydrated state" is in reference to the hydrogel core 26 being unable to imbibe additional water. Finally, the "partially hydrated state" is in reference to the hydrogel core 26 experiencing a hydration level or water content/expansion volume somewhere between the dehydrated state and the final hydrated state. By way of example, the hydrogel core 26 may have a water content of 5% in the dehydrated state, a water content of 85% in the final hydrated state, and a water content of 6%–84% in the partially hydrated state. As will be understood by one of ordinary skill in the art, the hydrogel core 26 generally expands in outer dimension(s) as the hydrogel core 26 transitions from the dehydrated state to the final hydrated state.

With the above definitions in mind, in one preferred embodiment, the prosthetic disc nucleus 22 is comprised of the hydrogel core 26 and the constraining jacket 28. The constraining jacket 28 is secured about the hydrogel core 26 by closures 30 located at opposite ends of the constraining jacket 28.

The preferred construction of the prosthetic disc nucleus 22, including the hydrogel core 26 and the constraining jacket 28, can assume a number of different shapes and sizes. Examples of acceptable constructions are provided in Ray et al., U.S. Pat. Nos. 5,824,093 and 6,132,465 the teachings of which are incorporated herein by reference. In general terms, the hydrogel core 26 is preferably formulated as a mixture of hydrogel polyacrylonitrile. In particular, an acrylamide/acrylonitrile block co-polymer is used. Alternatively, the hydrogel core 26 can be any hydrophilic acrylate derivative with a unique multi-block co-polymer structure or any other hydrogel material having the ability to deform and reform in a desired fashion in response to placement and removal of loads thereon. For example, the hydrogel core 26 can be formulated as a mixture of polyvinyl alcohol and water. Much like a normal disc nucleus, the hydrogel core 26 will initially swell from the dehydrated state as it absorbs fluid. When fully hydrated, the hydrogel core 26 will have a water content of 25%–90%. The hydrogel material used for the hydrogel core 26 in the preferred embodiment is manufactured under the trade name Hypan® by Hymedix International, Inc. of Dayton, N.J.

In addition to providing for varying water contents and volumes, the hydrogel core 26 material preferably allows the prosthetic disc nucleus 22 to be manufactured to assume different shapes in either the dehydrated state or the final hydrated state. For example, the hydrogel core 26 may be fabricated to have an elongated, rectangular shape in the dehydrated state shown in FIG. 1. Alternatively, the hydrogel core 26 may be angled, wedged, circular, etc. Even further, the hydrogel core 26 can be formed to assume an irregular shape, such as a shape corresponding generally with a shape of a disc nucleus. Due to a shape memory characteristic associated with many hydrogel materials, such as the preferred Hypan®, the hydrogel core 26 can be formed to assume and revert to a first shape in the final hydrated state and a second shape in the dehydrated state. For example, the hydrogel core 26 can be formed to assume a generally rectangular shape in the dehydrated state, subsequently hydrating and expanding to a tapered, wedged configuration in the final hydrated state.

Again, with reference to the one preferred embodiment of the prosthetic disc nucleus 22, the constraining jacket 28 is preferably a flexible tube made of tightly woven, high tenacity polymeric fabric. For example, in one preferred embodiment, high molecular weight polyethylene is used as the weave material for the constraining jacket 28. However, polyester or any other high tenacity polymeric material can be employed, and carbon fiber yarns, ceramic fibers, metallic fibers, etc., are also acceptable.

The constraining jacket 28 is preferably made of fibers that have been highly oriented along their length. As a result, the constraining jacket 28 material while flexible, has little elasticity or stretch. The constraining jacket 28 defines a generally fixed maximum volume including a generally fixed length (x-axis of FIG. 1). In one preferred embodiment, the generally fixed maximum volume of the constraining jacket 28 is less than a theoretical volume of the hydrogel core 26 if allowed to completely hydrate without constraint. Thus, because the hydrogel core 26 has a natural, fully hydrated volume greater than that of the constraining jacket 28, the constraining jacket 28 will be tight about the hydrogel core 26 in the final hydrated state.

The preferred woven construction of the constraining jacket 28 creates a plurality of small openings 32 (shown generally in FIG. 1). Each of the plurality of small openings 32 is large enough to allow hydration of the hydrogel core 26, but are small enough to prevent the hydrogel core 26 from escaping. Each of the plurality of small openings 32 preferably has an average diameter of 10 micrometers, although other dimensions are acceptable. In this regard, although the constraining jacket 28 has been described as having a woven configuration, any other configuration having a semi-permeable or porous attribute can be employed.

As described in greater detail below, following implantation, the constraining jacket 28 serves to constrain hydration and expansion of the hydrogel core in a predetermined, desired fashion. Alternatively, the prosthetic disc nucleus 22 can be configured to control, constrain and/or simply contain the hydrogel core 26 with components/structures different from the preferred constraining jacket 28. For example, the hydrogel core 26 can be disposed within a flexible, permeable bag having a volume slightly greater than a volume of a nucleus cavity into which the prosthetic disc nucleus 22 is implanted. Even further, the hydrogel core 26 can be contained within a more rigid structure. Even further, the hydrogel core 26 can be implanted without a separate enclosure body, such that the constraining jacket 28 is eliminated.

With the above description of the prosthetic disc nucleus 22 in mind, the retainer 24 is configured to selectively contain the prosthetic disc nucleus 22, constraining hydration of the hydrogel core 26 to a partially hydrated state. In one preferred embodiment, the retainer 24 includes opposing clamp bodies 40, 42 and an attachment device 44. The attachment device 44 releasably secures the clamp bodies 40, 42 about the prosthetic disc nucleus 22.

The clamp bodies 40, 42 are preferably identical, formed from a rigid, high-strength material such as stainless steel or aluminum. Alternatively, other rigid materials such as a structural polymer or ceramic are equally useful. Regardless, each of the clamp bodies 40, 42 forms a channel 46 and ports 48 (hidden for the clamp body 42). The channels 46 are formed in a corresponding fashion such that upon assembly of the clamp bodies 40, 42, a cavity 50 (shown best in FIG. 3) is defined. The cavity 50 is sized and shaped to receive the prosthetic disc nucleus 22. As such, the channels 46 are sized and shaped in accordance with a size and shape of the prosthetic disc nucleus 22, specifically in the dehydrated state.

The ports 48 extend through the clamp bodies 40, 42 to the respective channels 46. Thus, the ports 48 provide for passage of a hydration liquid (not shown) from outside of the retainer 24 into the cavity 50. In a preferred embodiment, at least one of the ports 48 is centrally positioned along the respective clamp body 40, 42 to facilitate fluid interaction with a central portion of the cavity 50. Further, the channels 46 are preferably formed to be open-ended, again to facilitate fluid interaction internally within the cavity 50. Alternatively, however, the channels 46 can be closed and/or additional ports added. While FIG. 1 depicts the clamp bodies 40, 42 as including a plurality of the ports 48, only a single port need be provided.

Figure 2:
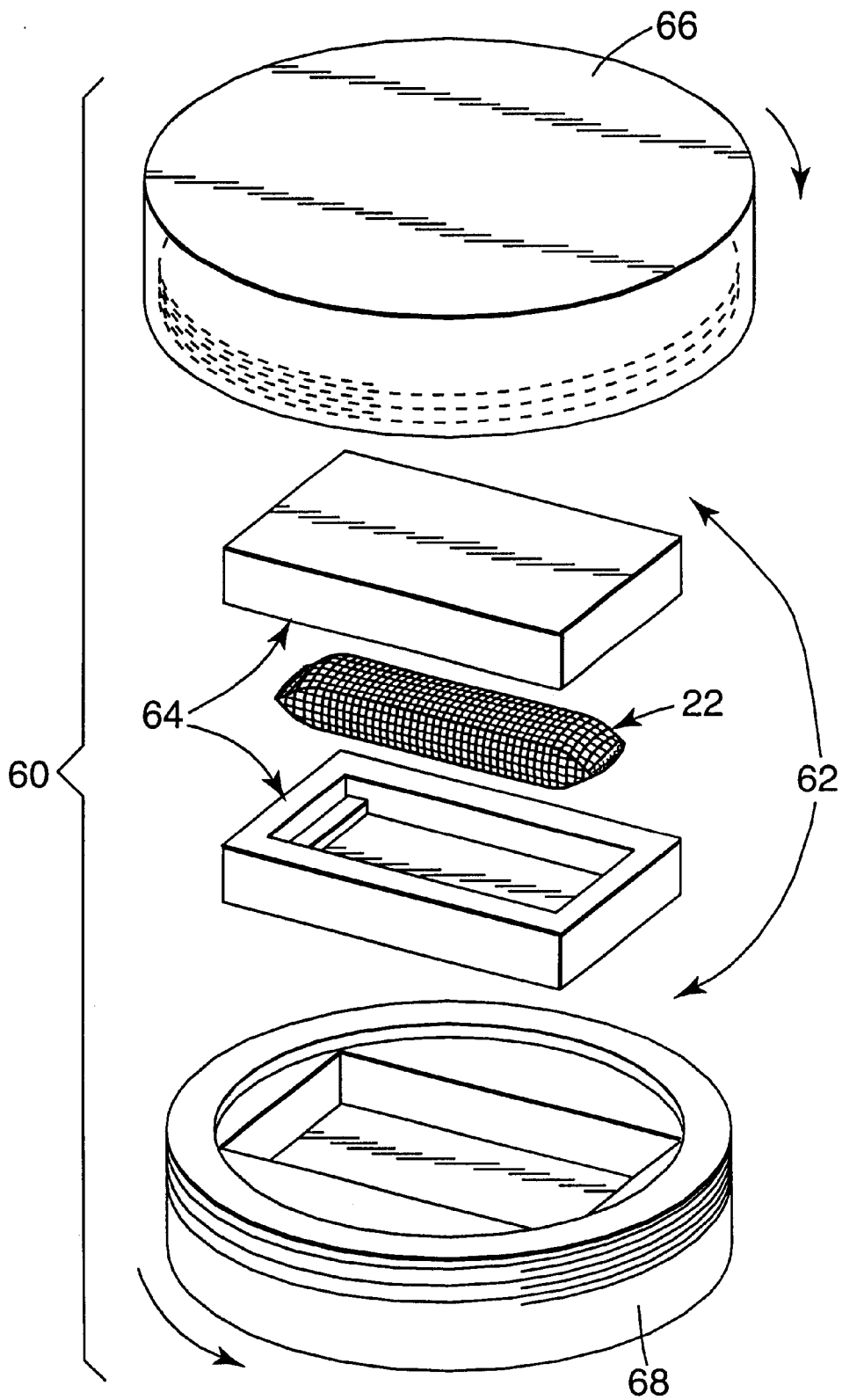
FIG. 2 is an exploded, perspective view of an alternative packaged prosthetic disc nucleus in accordance with the present invention.

The attachment device 44 releasably secures the clamp bodies 40, 42 to one another, and in one preferred embodiment includes a pair of screws. With this configuration, the screws pass through corresponding openings 52 in the first clamp body 40, and threadably engage threaded bores 54, respectively, in the second clamp body 42. Alternatively, the attachment device 44 can assume a wide variety of other forms. For example, the clamp bodies 40, 42 can be hingedly secured to one another in a clamshell configuration, with the attachment device 44 being configured to achieve a snap fit between the clamp bodies 40, 42. Alternatively, the first clamp body 40 can be sized to be frictionally received within extensions formed on the second clamp body 42. Regardless, the attachment device 44 secures the clamp bodies 40, 42 in a locked position and releases the first clamp body 40 from the second clamp body 42 in a released positioned whereby the prosthetic disc nucleus 22 is released and accessible by a user. For example, FIG. 2 depicts an alternative packaged prosthetic disc nucleus 60 that includes the prosthetic disc nucleus 22, and a retainer 62. The retainer 62 includes opposing clamp bodies 64 and first and second housing sections 66, 68. The first housing section 66 serves as a screw-top and is threadably securable to the second housing section 68. With this configuration, the housing sections 66, 68 serve as the attachment device, forcing the clamp bodies 64 to engage and constrain the prosthetic disc nucleus 22. Prior to use, the first housing section 66 can be unscrewed or otherwise decoupled from the second housing section 68, thereby releasing the prosthetic disc nucleus 22.

Returning to FIG. 1, upon final assembly and exposure to a hydration liquid, the prosthetic disc nucleus 22, and in particular, the hydrogel core 26, will hydrate within the cavity 50, thereby placing an expansion force onto an interior of the retainer 24. The retainer 24 is configured to statically resist this expansion force. In accordance with the one preferred embodiment of the prosthetic disc nucleus 22, the retainer 24 is configured to statically resist an expansion force in the range of 250–400 pounds. Alternatively, the retainer 24 can be configured to statically resist an even higher expansion force.

Construction of the packaged prosthetic disc nucleus 20 begins with formation of the prosthetic disc nucleus 22. In accordance with one preferred embodiment, the hydrogel core 26 is formed to have a predetermined shape in the hydrated state. For example, the hydrogel core 26 can be fabricated to have an elongated rectangular shape in the hydrated state. Alternatively, the hydrogel core 26 may be angled, tapered, wedged, circular, irregularly shaped, etc. in the hydrated state. Preferably, the hydrogel material is processed or oriented such that regardless of subsequent fabrication steps, the hydrogel core 26 will return to the predetermined shape upon subsequent dehydration and re-hydration to the final hydrated state.

Once formed, the hydrogel core 26 is placed within the constraining jacket 28. The closures 30 are then formed, for example with stitching, to secure the hydrogel core 26 within the constraining jacket 28.

Figure 3:
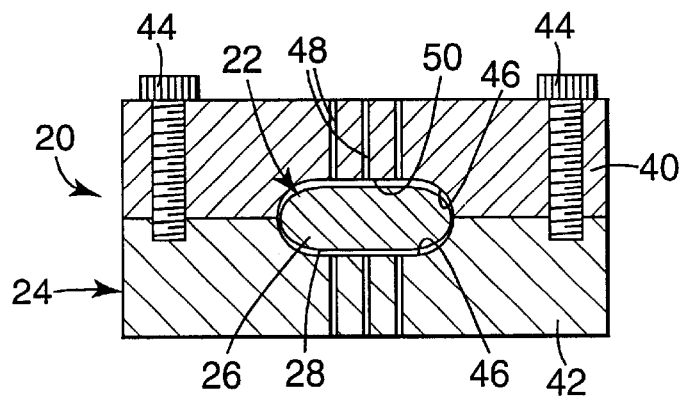
FIG. 3 is a front, cross-sectional view of the packaged prosthetic disc nucleus of FIG. 1 in a dehydrated state.

The prosthetic disc nucleus 22 is then dehydrated, preferably under compression. More particularly, in one preferred embodiment, the prosthetic disc nucleus 22 is located within a compression mold (not shown), and the entire assembly placed within an oven. As the hydrogel core 26 dehydrates within the oven, the compression mold forces the prosthetic disc nucleus 22 to a desired dehydrated shape in the dehydrated state. Once again, the dehydrated shape may or may not be identical to a shape in the hydrated state. The prosthetic disc nucleus 22, in the dehydrated state, is then placed within the retainer 24 as shown in FIG. 3. As should be apparent from FIG. 3, dehydration of the prosthetic disc nucleus 22 within the compression mold renders the prosthetic disc nucleus 22 to a size and shape slightly smaller than an available volume defined by the cavity 50. In other words, in the dehydrated state, the prosthetic disc nucleus 22 fits within the cavity 50. The attachment device 44 is then used to secure the clamp bodies 40, 42 about the prosthetic disc nucleus 22.

Figure 4:
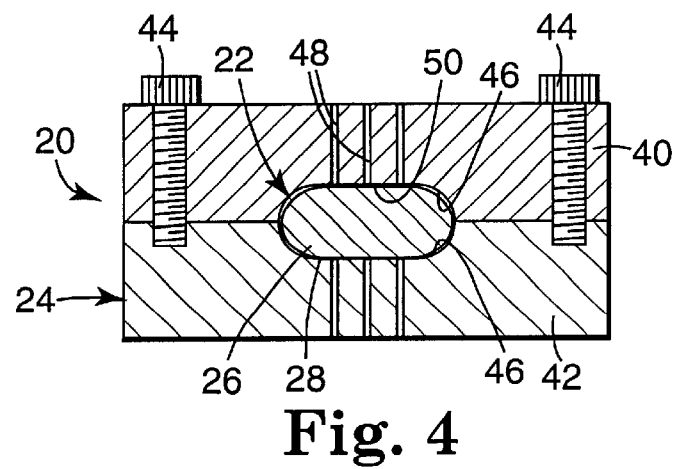
FIG. 4 is a front, cross-sectional view of the packaged prosthetic disc nucleus of FIG. 3 in a partially hydrated state.

The packaged prosthetic disc nucleus 20 can then be exposed to a hydration liquid, such as water or an appropriate water-based solution (e.g., Ringer's solution), and allowed to hydrate. With hydration, the hydrogel core 26 transitions from the dehydrated state depicted in FIG. 3 to the partially hydrated state shown in FIG. 4. As previously described, the retainer 24 constrains the prosthetic disc nucleus 22, preventing the hydrogel core 26 from attaining full hydration (or hydrating the final hydration state). Effectively, then, the retainer 24 constrains and maintains the hydrogel core 26 in the partially hydrated state. In one preferred embodiment, the retainer 22 constrains the hydrogel core 26 to a water content in the range of 20%–80% of the dehydrated weight in the partially hydrated state.

Figure 5:
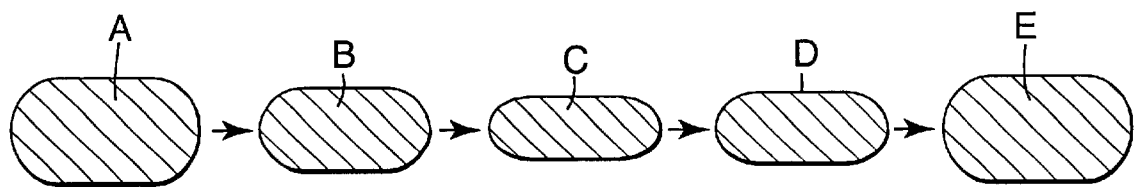
FIG. 5 is a side-by-side comparison of a hydrogel core portion of the prosthetic disc nucleus in accordance with the present invention at various hydration states.

As a point of reference, FIG. 5 illustrates the hydrogel core 26 (in cross-section) at various stages of manufacture/hydration. For example, the hydrogel core 26 is shown in the hydrated state following initial formation at A. If allowed to naturally dehydrate (e.g., exposed to air without any compressive forces), the hydrogel core 26 would assume the form depicted at B. However, as previously described, the hydrogel core 26 is preferably subjected to compressive forces during dehydration, such that the hydrogel core 26 assumes the form shown at C, which corresponds with the configuration shown in FIG. 3. Notably, the hydrogel core 26 is essentially incompressible such that a volume of the hydrogel core 26 in the dehydrated state is identical for both configurations B and C. However, the preferred compression reduces the height (Y-axis in FIG. 5) and width (Z-axis) of the hydrogel core 26 in configuration C. It will be understood that a length of the hydrogel core 26 will be increased at configuration C (as compared to B). When placed in contact with a hydration liquid, the hydrogel core 26 hydrates, constrained by the retainer 24 (FIG. 4) to the partially hydrated state shown at D (corresponding with the configuration of FIG. 4).

As illustrated in FIG. 5, the hydrogel core 26 in the partially hydrated state D is slightly larger (in terms of height and width) than the hydrogel core 26 in the compressed, dehydrated state C. However, the height and width of the partially hydrated state D is less than that of the naturally dehydrated configuration B. Finally, following removal from the retainer 24 and implant, the hydrogel core 26 hydrates to the hydrated state E (preferably constrained by the constraining jacket 28 (FIG. 1)), which is identical to the hydrated state A previously described. By way of example, and with reference to a "typical" disc space having a natural height of 9 mm, the hydrogel core 26 (constrained by the constraining jacket 28) will have a height of 9 mm in the hydrated state (A and E of FIG. 5). The naturally dehydrated hydrogel core 26 (B in FIG. 5) has a height of 7 mm. The compressed, dehydrated hydrogel core 26 (C in FIG. 5) has a height of 6 mm. Finally, the partially hydrated hydrogel core 26 (D in FIG. 7) has a height of 6.5 mm. As a result, the partially hydrated hydrogel core 26 (D) is more easily implanted than the naturally dehydrated hydrogel core B due to the reduction in height. Further, because the hydrogel core 26 is partially hydrated, it is much more pliable than in the dehydrated state, thereby minimizing the opportunity for migration.

Figure 6:
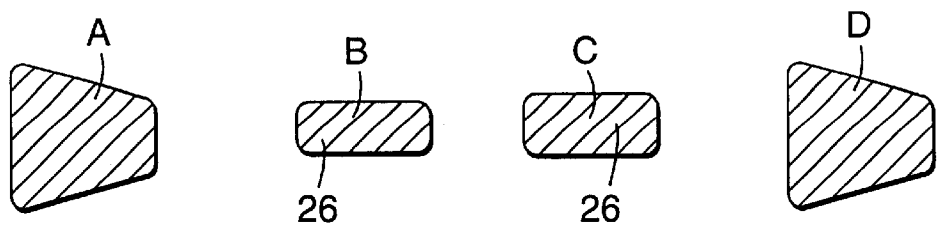
FIG. 6 illustrates the prosthetic disc nucleus in variable stages of hydration.

FIG. 6 illustrates another preferred characteristic of the prosthetic disc nucleus 22, and in particular the hydrogel core 26, whereby the hydrogel core 26 is configured to transition from a first shape in the dehydrated state to a second shape in the hydrated state. More particular, the hydrogel core 26 is shown as being formed to have a wedge shape in the hydrated state A. At B, the hydrogel core 26 is compressed to a different shape in the dehydrated state. The partially hydrated state C, in which the hydrogel core 26 is partially hydrated within the retainer 24 (FIG. 4), generally corresponds in shape with the dehydrated state shape B. Finally, following removal from the retainer 24 and implantation, the hydrogel core 26 hydrates back to the shape of the hydrated state at D.

Figure 7:
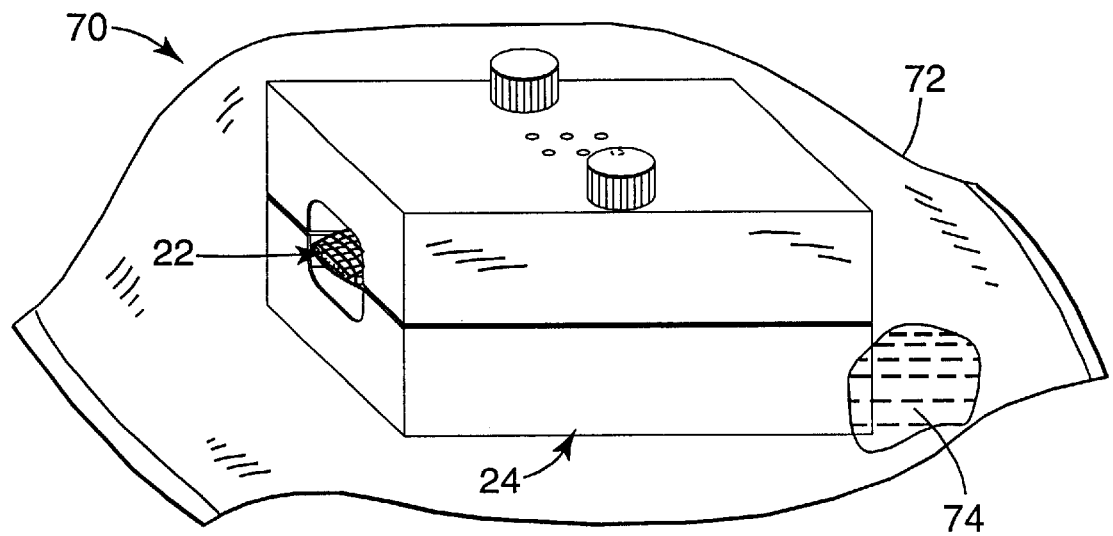
FIG. 7 is a perspective view of an alternative packaged prosthetic disc nucleus in accordance with the present invention.

Partial hydration of the prosthetic disc nucleus 22 within the retainer 24 can be accomplished in a wide variety of fashions, such as simply placing the packaged prosthetic disc nucleus 20 within a volume of appropriate liquid. Thus, the packaged prosthetic disc nucleus 20 can be provided to a surgeon who subsequently places the assembly 20 into a volume of hydration liquid. Alternatively, the packaged prosthetic disc nucleus can be provided to the surgeon in the partially hydrated state. For example, an alternative embodiment packaged prosthetic disc nucleus 70 is shown in FIG. 7. The packaged prosthetic disc nucleus 70 is similar to the packaged prosthetic disc nucleus 20 (FIG. 1) previously described, and includes the prosthetic disc nucleus 22 and the retainer 24. In addition, the packaged prosthetic disc nucleus 70 includes a sealed enclosure or pouch 72 containing the retainer 24/prosthetic disc nucleus 22 and a hydration liquid (shown generally at 74).

The pouch 72 is preferably formed of metalisized polyester, but may alternatively be any other known plastic, sealable film material. Further, it is preferred that the packaged prosthetic disc nucleus 70 be amenable to sterilization. The pouch 72 is preferably impermeable to maintain the hydration liquid 74 and can be sealed about the various components by known adhesive bonding or heat bonding techniques. While the pouch or enclosure 72 has been depicted as being relatively flexible, a more rigid structure can alternatively be employed. For example, the pouch or enclosure 72 can be a box-like body formed from metal or hardened plastic.

The hydration liquid 74 is selected for hydrating the hydrogel core 26. As such, the hydration liquid 74 is preferably water, but other liquid solutions are equally acceptable such as Ringer's solution, etc.

Figure 8:
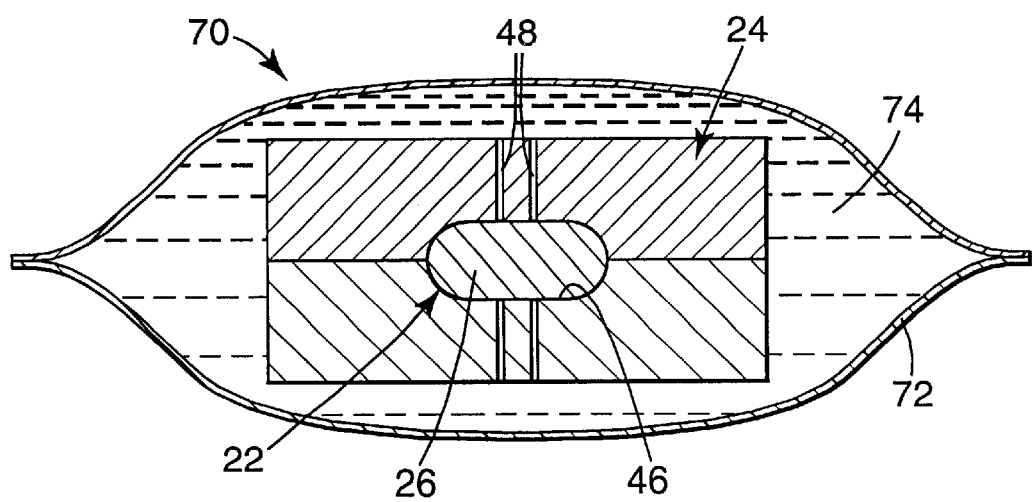
FIG. 8 is a cross-sectional view of the packaged prosthetic disc nucleus of FIG. 7.
Figure 9:
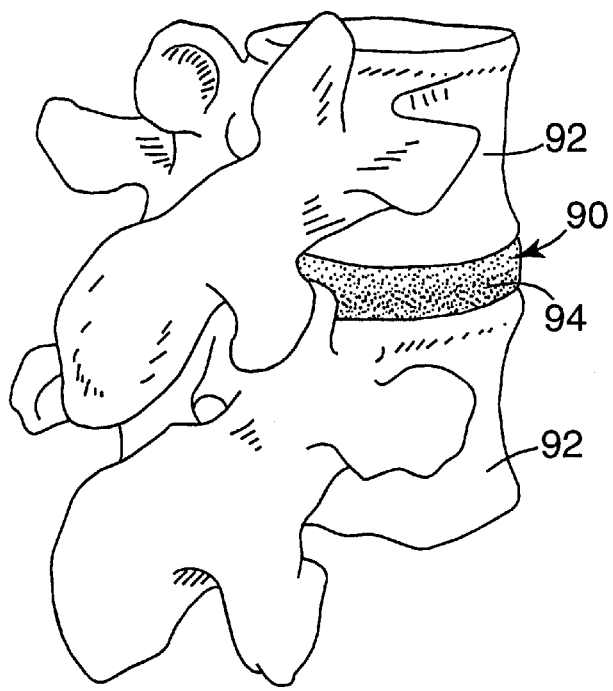
FIG. 9 is a posterior view of a spinal segment including a discal area.
Figure 10:
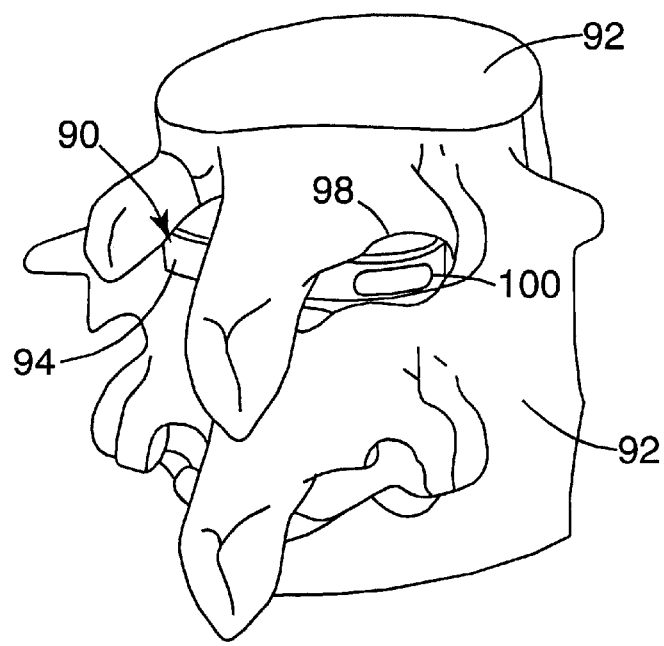
FIG. 10 is a posterior view of the spinal segment of FIG. 9 depicting an incision through an anulus.

As best shown in FIG. 8, the hydration liquid 74 within the pouch 72 interacts with, and is imbibed by, the hydrogel core 26 via the open-ended channels 46 and the ports 48 formed by the retainer 24. It will be recalled that the retainer 24 need not necessarily be open-ended, and that only a single port 48 need be included.

As previously described, the exact form of the prosthetic disc nucleus 22 may be vary greatly from the preferred embodiments shown in FIGS. 1–8. Regardless of the exact shape or construction, however, the preferred method of use and implantation is identical. For example, FIGS. 9–12 depict implantation of the prosthetic disc nucleus 22 (FIG. 1) into a damaged disc space 90. The disc space 90 separates adjacent vertebrae 92 and includes an anulus 94 and a nucleus region or cavity 96 (shown best in FIG. 11). Proper positioning is achieved by first performing a laminectomy in a targeted lamina area 98. A passage 100 is created through a posterior side of the anulus 94, either by simple incision or removal of a radial tissue plug. If necessary, nucleus material is removed from the nucleus cavity 96 to create room for the prosthetic disc nucleus 22. Although in this example a single passage 100 is illustrated and discussed, a pair of passages may alternatively be used. Further, while a generally posterior technique has been identified, insertion through any portion of the anulus 94 is acceptable.

With the disc space 90 properly prepared, the packaged prosthetic disc nucleus 20, 70 is then provided. For example, with reference to the preferred packaged prosthetic disc nucleus 70 shown in FIG. 7, the packaged prosthetic disc 70 includes the prosthetic disc nucleus 22 maintained in the partially hydrated state by the retainer 24. In a sterile environment, the pouch 72 is opened, and the retainer 24/prosthetic disc nucleus 22 removed. The prosthetic disc nucleus 22 is then removed from the retainer 24 by separating the clamp bodies 40, 42.

Once removed, the prosthetic disc nucleus 22 is, in the partially hydrated state, implanted into the disc space 90 via the passage 100. In this regard, the passage 100 may require minor dilation to facilitate insertion of the prosthetic disc nucleus 22. Notably, however, in the partially hydrated state, the prosthetic disc nucleus 22 has a height that is less than a height of the anulus 94 such that any requisite dilation will be minimal. Further, because the prosthetic disc nucleus 22 and in particular, the hydrogel core 26, is compressed prior to implant, the prosthetic disc nucleus 22 will have a height that is less than a height of the hydrogel core 26 if "naturally" dehydrated. Thus, although the hydrogel core 26 is partially hydrated, the prosthetic disc nucleus 22 will more easily fit within the passage 100 than would a similarly constructed prosthetic disc nucleus in which the hydrogel core was simply dehydrated.

Figure 11:
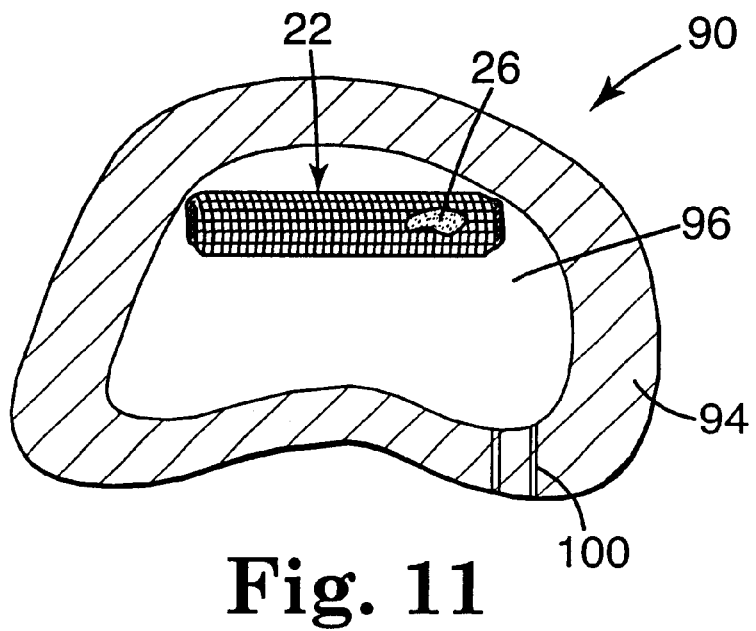
FIG. 11 is a top, sectional view of a human disc space having a prosthetic disc nucleus implanted.

Following complete insertion within the anulus 94 the prosthetic disc nucleus 22 is rotated approximately 90° or otherwise positioned as shown in FIG. 11. Where desired, a second prosthetic disc nucleus 102 (FIG. 12) may similarly be implanted and positioned posterior of the prosthetic disc nucleus 22. Additional nuclei can also be implanted, it being understood that as few as one prosthesis is required.

Once positioned, the hydrogel core 26 hydrates. In this regard, the nucleus cavity 96 may be flushed with an appropriate hydration liquid, such as Ringer's solution, to promote rapid hydration. Regardless, because the prosthetic disc nucleus 22 is partially hydrated, the hydrogel core 26 will reach the final hydrated state more rapidly than would a dehydrated prosthetic disc nucleus. Further, the hydrogel core 26 exhibits a relatively high degree of conformability in the partially hydrated state (as compared to the relatively hard attribute associated with the dehydrated state). Thus, unlike prior hydrogel-based prostheses that are implanted in the dehydrated state, the prosthetic disc nucleus 22 will readily frictionally engage the end plates of the opposing vertebrae 92. As a result, when the disc space 90 is under load and/or the adjacent vertebrae 92 are flexed relative to one another, the prosthetic disc nucleus 22 will remain stationary, unlike a hard, dehydrated prosthesis.

Figure 12:
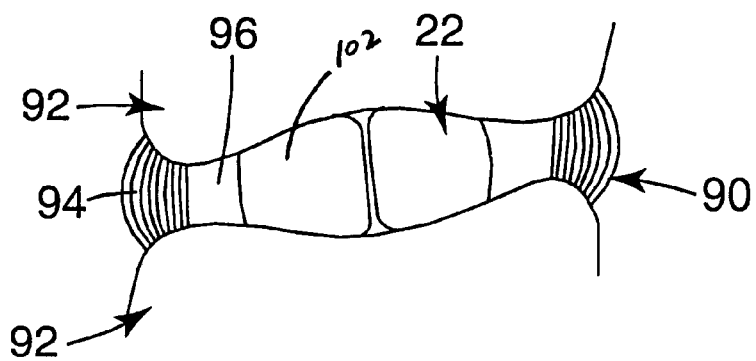
FIG. 12 is a side, cross-sectional view of the disc space of FIG. 11, depicting the prosthetic disc nucleus in a final hydrated state.

With hydration, the prosthetic disc nucleus 22, 102 supports and separates the adjacent vertebrae 92 as shown in FIG. 12, restoring the anulus 94 to its natural height.

Figure 13:
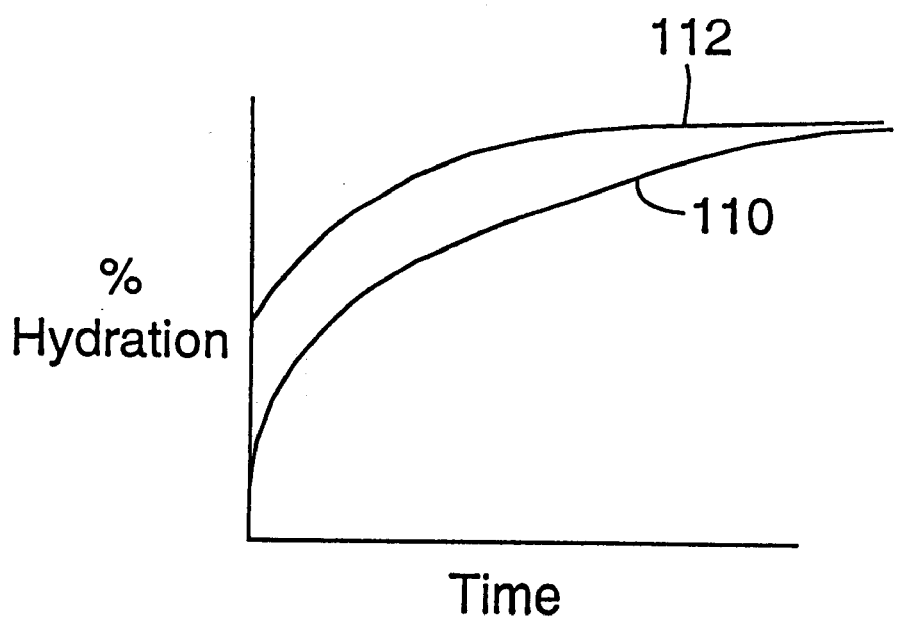
FIG. 13 is a graph illustrating time of hydration for a prosthetic disc nucleus packaged in accordance with the present invention as compared to a prior art hydrophilic prosthetic disc nucleus.

By providing the prosthetic disc nucleus 22 in a partially hydrated state, the packaged prosthetic disc nucleus 20, 70 of the present invention provides a distinct advantage over prior art hydrogel-based (or hydrophilic) prostheses that are implanted in a dehydrated state. For example, FIG. 13 illustrates graphically the hydration percentage over time for both a prior art hydrogel-based prosthetic disc nucleus (represented by the curve 110) and a partially hydrated prosthetic disc nucleus in accordance with the present invention (represented by the curve 112). The partially hydrated prosthetic disc nucleus curve 112 approaches the final hydrated state more quickly than the dehydrated prosthetic disc nucleus curve 110. As a result, vertebral support will be more immediately provided, and also the time frame in which undesired prosthesis migration and/or explant is reduced. Further, because the partially hydrated prosthetic disc nucleus is partially hydrated at implant, the prosthesis is more compliant, and therefore more likely to frictionally engage the end plate(s), again minimizing the opportunity for migration.

Figure 14:
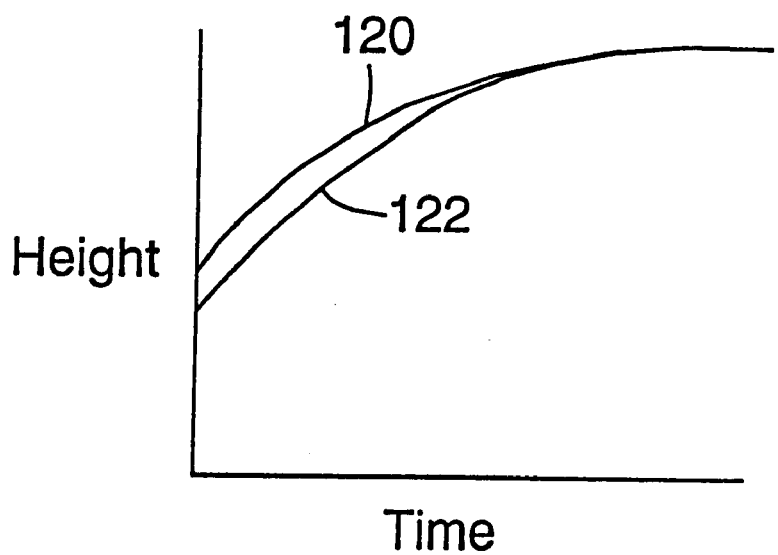
FIG. 14 is a graph depicting change in height of a prosthetic disc nucleus packaged in accordance with the present invention as compared to a prior art hydrophilic prosthetic disc nucleus.

An additional advantage of the preferred packaged prosthetic disc nucleus 20, 70 is best described with reference to the graph of FIG. 14. FIG. 14 provides a comparison of the change in height over time of a hydrogel-based prosthetic disc nucleus implanted in a dehydrated state (represented by the curve 120) and that of the prosthetic disc nucleus 22 (FIG. 1) implanted in a partially hydrated state (represented by the curve 122). As previously described, the prosthetic disc nucleus 22 is preferably flattened to a height smaller than that otherwise found with a naturally dehydrated device. As such, the partially hydrated curve 122 initially has a height less than a height of the prior art curve 120. Over time, however, the partially hydrated curve 122 attains the same height as the prior art dehydrated curve 120. Thus, the partially hydrated prosthetic disc nucleus 22 of the present invention will hydrate to the same height as a hydrogel-based prosthetic disc nucleus implanted in a dehydrated state. However, because the preferred prosthetic disc nucleus 22 is flattened prior to implant, a smaller opening in the anulus is required. Similarly, due to the flattened nature of the prosthetic disc nucleus 22, a larger sized body can be implanted as compared to a "standard" hydrogel-based prosthetic disc nucleus. That is to say, because the partially hydrated prosthetic disc nucleus 22 of the present invention is, upon initial implant, smaller in height and width than a corresponding dehydrated volume of a prior art hydrophilic prosthetic disc nucleus, a surgeon is able to implant a prosthesis that is as large as possible. As a result, the opportunities for migration following implant are greatly reduced.

The packaged prosthetic disc nucleus of the present invention provides a marked improvement over previous designs. First, by providing a prosthetic disc in a partially hydrated state, following implant the prosthetic disc nucleus will approach full hydration more rapidly than prior art hydrogel-based prosthetic disc nucleus devices implanted in a dehydrated state. As a result, required disc space support and separation is experienced on an expedited basis. Additionally, and in one preferred embodiment, the packaged prosthetic disc nucleus provides the prosthesis in a flattened state. This preferred configuration facilitates implantation through a small anulus opening and ensures that a sufficiently sized prosthesis will be selected by a surgeon. This, in turn, reduces the opportunity for migration.

Although the present invention has been described with reference to preferred embodiments, workers skilled in the art will recognize that changes may be made in form and detail without departing from the spirit and scope of the present invention. For example, the packaged prosthetic disc nucleus has been preferably described as providing a prosthetic disc nucleus sized to be implanted in pairs within a disc space. Alternatively, however, a wide variety of other shapes and sizes may be provided such that a single prosthesis provides necessary disc support, or multiple prostheses are implanted.

What is claimed is:

1. A packaged prosthetic disc nucleus apparatus comprising:
   a prosthetic disc nucleus for implantation within a nucleus cavity defined by an anulus and opposing end plates, the prosthetic disc nucleus including:
      a hydrogel core configured to hydrate from a dehydrated state,
      wherein the prosthetic disc nucleus is configured such that following implantation, the hydrogel core hydrates to a final hydrated state; and
   a retainer selectively containing the prosthetic disc nucleus, the retainer configured to allow the hydrogel core, upon contact with a hydration liquid, to hydrate from the dehydrated state and prevent the hydrogel core from hydrating to the final hydrated state, such that the prosthetic disc nucleus is constrained by the retainer in a partially-hydrated state, and wherein the retainer is configured to release the prosthetic disc nucleus for subsequent implantation of the prosthetic disc nucleus into the nuceus cavity.

2. The apparatus of claim 1, wherein the prosthetic disc nucleus further includes a jacket surrounding the hydrogel core, the jacket constraining hydration of the hydrogel core to the final hydrated state.

3. The apparatus of claim 2, wherein the jacket is substantially inelastic, defining a volume less than a volume of the nucleus cavity.

4. The apparatus of claim 1, wherein the retainer is configured such that water content of the hydrogel core in the partially-hydrated state is in the range of 20%–80% of the water content in the final hydrated state.

5. The apparatus of claim 4, wherein the water content in the partially-hydrated state is approximately 50% of the water content in the final hydrated state.

6. The apparatus of claim 1, wherein the prosthetic disc nucleus expands to a final height in the final hydrated state, and further wherein the retainer is configured to constrain the prosthetic disc nucleus to a partially-hydrated height that is less than the final height.

7. The apparatus of claim 1, wherein the prosthetic disc nucleus has a first height in a naturally dehydrated state, and further wherein the retainer is sized to constrain the prosthetic disc nucleus to a partially hydrated height that is less than the first height.

8. The apparatus of claim 1, wherein the retainer forms at least one port for allowing passage of liquid into contact with the prosthetic disc nucleus.

9. The apparatus of claim 8, wherein the prosthetic disc nucleus includes opposing ends and a central portion, and further wherein at least one of the ports is positioned to allow fluid interaction with the central portion of the prosthetic disc nucleus.

10. The apparatus of claim 1, wherein the retainer is configured to maintain integrity in response to an internal expansion force generated by the prosthetic disc nucleus.

11. The apparatus of claim 10, wherein the retainer is configured to substantially resist an internal expansion force of at least 250 pounds.

12. The apparatus of claim 1, wherein the retainer includes opposing clamp bodies forming a cavity sized to receive the prosthetic disc nucleus and an attachment device for selectively securing the opposing clamp bodies.

13. The apparatus of claim 12, wherein the attachment device includes opposing housing sections threadably securable to one another, the opposing housing sections being sized to encompass the clamp bodies and the prosthetic disc nucleus.

14. The apparatus of claim 1, further comprising:
an outer enclosure surrounding the retainer; and
a hydration liquid contained within the enclosure for hydrating the hydrogel core.

15. A packaged prosthetic disc nucleus apparatus comprising:
a prosthetic disc nucleus for implantation within a nucleus cavity defined by an anulus and opposing end plates, the prosthetic disc nucleus including:
a hydrogel core configured to hydrate and expand from a dehydrated height,
wherein the prosthetic disc nucleus is configured such that following implantation, the hydrogel core expands to a final hydration height; and
a retainer selectively containing the prosthetic disc nucleus, the retainer configured to constrain the hydrogel core, upon contact with a hydration liquid, to a partial hydration height, the partial hydration height being less than the final hydration height, and wherein the retainer is configured to release the prosthetic disc nucleus for subsequent implantation of the prosthetic disc nucleus into the nucleus cavity.

16. The apparatus of claim 15, wherein the prosthetic disc nucleus further includes a jacket surrounding the hydrogel core, the jacket constraining the expansion of hydrogel core to the final hydration height.

17. The apparatus of claim 16, wherein the jacket is substantially inelastic, defining a volume less than a volume of the nucleus cavity.

18. The apparatus of claim 15, wherein the retainer forms a plurality of ports for allowing passage of liquid into contact with the prosthetic disc nucleus.

19. The apparatus of claim 18, wherein the prosthetic disc nucleus includes opposing ends and a central portion, and further wherein at least one of the plurality of ports is positioned to allow fluid interaction with the central portion of the prosthetic disc nucleus.

20. The apparatus of claim 15, wherein the retainer includes opposing clamp bodies combining to form a cavity sized to receive the prosthetic disc nucleus, and an attachment device for selectively securing the opposing clamp bodies.

21. The apparatus of claim 20, wherein the retainer is formed to substantially resist an internal expansion force of at least 250 pounds.

22. The apparatus of claim 20, wherein the attachment device includes opposing housing sections threadably securable to one another, the opposing housing sections being sized to encompass the clamp bodies and the prosthetic disc nucleus.

23. The apparatus of claim 15, further comprising:
an outer enclosure surrounding the retainer; and
a hydration liquid contained within the enclosure for hydrating the hydrogel core.

24. A method of packaging a prosthetic disc nucleus including a hydrogel core configured to hydrate from a dehydrated level to a final hydration level, the method comprising:
dehydrating the hydrogel core;
providing a retainer forming a cavity sized to selectively contain the prosthetic disc nucleus, wherein the retainer is configured to release the prosthetic disc nucleus for subsequent implantation of the prosthetic disc nucleus into the nucleus cavity;
placing the dehydrated prosthetic disc nucleus within the retainer;
exposing the prosthetic disc nucleus to a hydration liquid such that the hydrogel core hydrates; and
constraining hydration of the hydrogel core with the retainer to a partial hydration level that is less than the final hydration level.

25. The method of claim 24, wherein constraining hydration of the hydrogel core includes limiting the partial hydration level to a range of 20%–80% of the final hydration level.

26. The method of claim 25, wherein the partial hydration level is approximately 50% of the final hydration level.

27. The method of claim 24, wherein dehydrating the hydrogel core includes flattening the hydrogel core as the hydrogel core dehydrates.

28. The method of claim 24, wherein flattening the hydrogel core results in the hydrogel core having a height that is at least approximately 0.5 mm less than a naturally dehydrated height.

29. The method of claim 24, further comprising:
providing an outer enclosure;
placing the combination retainer and prosthetic disc nucleus within the outer enclosure;
at least partially filling the outer enclosure with a hydration liquid for hydrating the hydrogel core; and
sealing the outer enclosure.

* * * * *